United States Patent [19]

Houpis et al.

[11] Patent Number: 5,489,685
[45] Date of Patent: Feb. 6, 1996

[54] METHOD OF SYNTHESIZING FURO[2,3-B]PYRIDINE CARBOXYLIC ACID ESTERS

[75] Inventors: Ioannis Houpis, Plainfield; Audrey Molina, Ocean; Joseph E. Lynch, Plainfield; Hywyn R. O. Churchill, Westfield; Ralph P. Volante, Cranbury; Paul J. Reider, Westfield; Woo-Baeg Choi, No. Brunswick, all of N.J.

[73] Assignee: Merck & Co., Ltd., Rahway, N.J.

[21] Appl. No.: 241,818

[22] Filed: May 12, 1994

[51] Int. Cl.$^6$ .............................................. C07D 491/048
[52] U.S. Cl. ................................ 546/115; 546/116
[58] Field of Search ........................... 546/115, 116

[56] References Cited

U.S. PATENT DOCUMENTS

| | | | |
|---|---|---|---|
| 4,920,226 | 4/1990 | Los et al. ................................. | 546/115 |
| 5,413,999 | 5/1995 | Vacca et al. .......................... | 514/231.5 |

OTHER PUBLICATIONS

Sakamoto et al., Chem. Pharm. Bull., vol. 34 (7) pp. 2719–2724 (1986).
R. Heck, ". . . Palladium–catalyzed Vinylation Of Organic Halides . . . " Organic Reactions, Chapter, 2, pp. 345–391 (1981).
J. Reisch et al. J. Heterocyclic Chem., 28, 167 (Jan. 1991).
J. Reisch et al. Liebigs Ann. Chem. 1988, 69–73.
D. Wensbo et al. ". . . Palladium–Catalysed Synthesis . . . " Tetrahedron Letters, vol. 34, No. 17, pp. 2823–2826, 1993.
T. Jeschke et al. ". . . A Novel Approach to Bz–Substituted . . . " Tetrahedron Letters, vol. 34, No. 40, pp. 6471–6474, 1993.
D. Grotjahn et al. ". . . Cobalt–Mediated [2+2+] . . . " Synthesis, pp. 579–593, Jun. 1993.
C. E. Castro et al. ". . . Copper (1) Substitutions . . . " Journal of the American Chemical Society, 91:23, pp. 6464–6470, Nov. 5, 1968.
R. D. Stephens et al. "Substitution of Aryl Iodides . . . " J. Org. Chem., vol. 28, Dec., 1963.
C. E. Castro et al. ". . . Indoles, Benzofurans, Phthalides . . . " J. Org. Chem., vol. 31, pp. 4071–4077, Dec. 1966.
F. G. Schreiber et al. ". . . Synthesis of Benzofuran . . . " J. C. S. Perkin I, pp. 1514–1518, (1976).
R. Robinson, et al. . . . "Some Derivatives of 3–Ethylpyridine . . . " (1934), pp. 1536–1543.
J. W. McFarland et al. . . . "Synthesis of Furo . . . " Synthesis, vol. 8, pp. 735–737, Oct. 1971.
H. Sliwa, . . . "No. 113. Synthese de nouveaus . . . " Bulletin De La Societe Chimique De France, 1970, No. 2 pp. 646–652.
M. Robbins et al. . . . "Nucleic Acid Related Compounds . . . " J. Org. Chem., 1983, 48, pp. 1854–1862.
F. W. Hobbs et al. . . . "Palladium–Catalyzed Synthesis . . . " J. Org. Chem. 1989, 54, pp. 3420–3422.
A. P. VanSickle et al. . . . "Azapsoralens. Synthesis of . . . " J. Org. Chem. 1990, 55, 895–901.
H. R. Synder et al. . . . "A New Synthesis of Furo . . . " vol. 3, pp. 202–205 (Jun. 1966).

Primary Examiner—Bernard Dentz
Attorney, Agent, or Firm—Roy D. Meredith; Jack L. Tribble

[57] ABSTRACT

A process is disclosed for rapid synthesis of substituted furanyl pyridines.

5 Claims, No Drawings

METHOD OF SYNTHESIZING FURO[ 2,3-B] PYRIDINE CARBOXYLIC ACID ESTERS

BACKGROUND OF THE INVENTION

The present application is related to U.S. Ser. No. 08/059,038, filed May 7, 1993, now U.S. Pat. No. 5,413,999, U.S. Ser. No. 08/163,013 filed Dec. 15, 1993, now abandoned and U.S. Ser. No. 08/170,475 filed Dec. 12, 1993, now abandoned.

The present invention is concerned with a novel intermediate and process for synthesizing compounds which inhibit the protease encoded by human immunodeficiency virus (HIV), and in particular certain oligopeptide analogs, such as Compound K in the Examples below. These compounds are of value in the prevention of infection by HIV, the treatment of infection by HIV and the treatment of the resulting acquired immune deficiency syndrome (AIDS). These compounds are also useful for inhibiting renin and other proteases.

The invention described herein concerns a process to effect the synthesis of a substituted furanylpyridylmethylene side chain of a potent HIV protease inhibitor. A halopyridone is coupled with a substituted acetylene to give desired furanyl pyridine product in one or two steps. The process described is superior to prior art in that the process is shorter, more productive, less expensive and has higher yields with less environmental impact.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313, 277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)]. The end product compounds, including certain oligopeptide analogs that can be made from the novel intermediates and processes of this invention, are inhibitors of HIV protease, and are disclosed in EPO 541,168, which published on May 12, 1993. See, for example, Compound J therein, also illustrated in the Examples below.

The present application discloses an improved process to make a furanylpyridylmethylene side chain of the structure

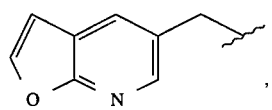

which is a new sidechain substituting for the pyridylmethylene group of Compound J. The resulting Compound K requires substantially similar synthesis as Compound J. Compound K is also a potent inhibitor of HIV protease.

Previous attempts to synthesize the furanylpyridyl methylene side chain involved a 10-step synthesis including several high temperature reactions, low overall yields and were difficult to scale-up. The present process reduces the number of steps to one or two, and requires smaller quantities of catalyst, e.g. $Cu^{II}$. Also, the present process utilitizes smaller quantities of organic solvents and proceeds in greater overall yield than prior methods, a result providing lower environmental impact than prior methods.

BRIEF DESCRIPTION OF THE INVENTION

The present invention provides new methods to effect the synthesis of substituted furanylpyridine derivatives in one or two steps. The process comprises coupling of halopyridone derivatives with a substituted acetylene, followed by cyclization. The product compounds are intermediates for compounds useful in the synthesis of inhibitors of HIV protease, renin and other proteases, e.g. Compound K.

DETAILED DESCRIPTION OF THE INVENTION

The present invention provides new methods for making substituted furanyl pyridine of formula I:

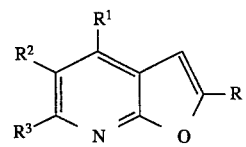

wherein

R is any protecting group selected from trimethylsilyl, $C_{1-4}$alkyl, $C_{1-4}$-alkoxy-$C_{1-4}$-alkoxy-$C_{1-4}$alkyl, aryl $C_{3-8}$cycloalkyl, heterocycle, —O—$R_x$, —N—$(R_x)_2$, or —S—$R_x$ wherein $R_x$ is $C_{1-4}$alkyl, aryl or heterocycle; and $R^1$ and $R^2$ and $R^3$ are independently selected from H, $C_{1-4}$ alkyl, aryl, OR', SR', $SiR_3$, $NR_2$,

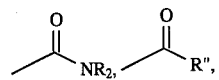

wherein

R' is H, $C_{1-4}$ alkyl or aryl;

R" is $C_{1-4}$ alkyl, aryl, SR' or $SiR_3$;

said process comprising the steps of (a) providing one equivalent of the 2-hydroxy pyridine of the formula

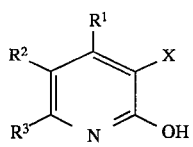

wherein X is Br, I, Cl, OSO$_2$CF$_3$, OSO$_2$F, or OPO$_2$R;

(b) reacting the pyridine of Step (a) with 1.0 or more equivalents of the acetylene

in the presence of catalyst selected from one or more of Cu$^I$, Cu$^{II}$, Pd$^O$, Pd$^{II}$, Pt$^O$, Pt$^{II}$, Ni$^O$, or Ni$^{II}$, in 1.0 or more equivalents of base and in solvent, at a temperature between about 25° C. and about 60° C., for a period of between about 30 minutes and about 48 hours;

(c) to give the compound of formula I

In one embodiment of this invention, there is an additional heating step near the end of the process. In this embodiment, the process for synthesizing a substituted furanyl pyridine of formula I:

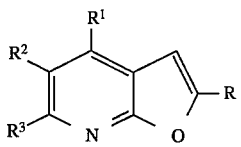

wherein

R is any protecting group selected from trimethylsilyl, C$_{1-4}$alkyl, C$_{1-4}$-alkoxy-C$_{1-4}$alkyl, aryl, C$_{3-8}$cycloalkyl, heterocycle, —O—R$_x$, —N—(R$_x$)$_2$, or —S—R$_x$ wherein R$_x$ is C$_{1-4}$alkyl, aryl or heterocycle; and R$^1$ and R$^2$ and R$^3$ are independently selected from H, C$_{1-4}$ alkyl, aryl, OR', SR', SiR$_3$, NR$_2$,

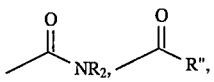

wherein

R' is H, C$_{1-4}$ alkyl or aryl;

R" is C$_{1-4}$ alkyl, aryl, SR' or SiR$_3$;

comprises the steps of (a) providing one equivalent of the 2-hydroxy pyridine of the formula

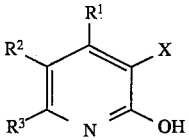

wherein X is Br, I, Cl OSO$_2$CF$_3$, OSO$_2$F, or OPO$_2$R;

(b) reacting the pyridine of Step (a) with 1.0 or more equivalents of the acetylene

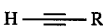

in the presence of catalyst selected from one or more of Cu$^I$, Cu$^{II}$, Pd$^O$, Pd$^{II}$, Pt$^O$, Pt$^{II}$, Ni$^O$, or Ni$^{II}$, in 1.0 or more equivalents of base and in solvent, at a temperature between about 25° C. and about 60° C., for a period of between about 30 minutes and about 48 hours, to give an intermediate;

(c) heating the intermediate at a temperature between about 25° C. and about 60° C. for a period of between about 30 minutes and about 48 hours;

(d) to give the compound of formula I.

In another embodiment of this invention relating to the trimethylsilyl protecting group, the process for synthesizing a substituted furanyl pyridine of formula II:

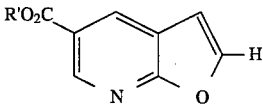

wherein

R' is C$_{1-4}$alkyl, or aryl;

comprises the steps of (a) providing one equivalent of the halogenated pyridine of the formula

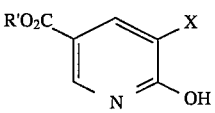

wherein X is Br, I, or Cl;

(b) reacting the halogenated pyridine of Step (a) with 1.0 or more equivalents of the acetylene

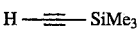

in the presence of catalyst selected from one or more of Cu$^I$, Cu$^{II}$, Pd$^O$, Pd$^{II}$, Pt$^O$, Pt$^{II}$, Ni$^O$, or Ni$^{II}$, in 1.0 or more equivalents of base and in ethereal or alcoholic solvent, at a temperature between about 25° C. and about 60° C., for a period of between about 30 minutes and about 48 hours;

(c) isolating the product

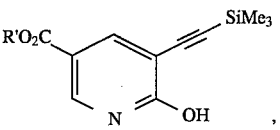

(d) reacting the product of Step (c) with any organic acid or mineral acid in ethereal solvent or in alcoholic solvent, at a temperature between about 25° C. and about 75° C. for an incubation time of between about 30 minutes and about 48 hours;

(e) treating with strong base or halide, at a temperature range of between about 25° C. and about 75° C. for an incubation time of between about 15 minutes and about 24 hours, to give a compound of formula II.

In another embodiment of this invention relating to the trimethylsilyl protecting group, the process for synthesizing a substituted furanyl pyridine of formula II:

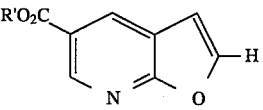

wherein

R' is C$_{1-4}$alkyl, or aryl;

comprises the steps of (a) providing one equivalent of the halogenated pyridine of the formula

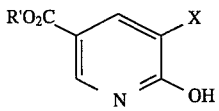

wherein X is Br, I, or Cl;

(b) reacting the halogenated pyridine of Step (a) with 1.0 or more equivalents of the acetylene

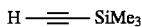

in the presence of catalyst selected from one or more of $Cu^I$, $Cu^{II}$, $Pd^0$, $Pd^{II}$, $Pt^0$, $Pt^{II}$, $Ni^0$, or $Ni^{II}$, in 1.0 or more equivalents of base and in ethereal or alcoholic solvent, at a temperature between about 25° C. and about 60° C., for a period of between about 30 minutes and about 48 hours;

(c) isolating the product

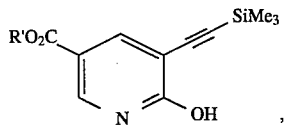

(d) reacting the product of Step (c) with a catalyst selected from $Cu^I$, $Cu^{II}$ or $Pd^{II}$ in ethereal solvent or in alcoholic solvent, at a temperature between about 25° C. and about 75° C. for an incubation time of between about 30 minutes and about 48 hours;

(e) treating with strong base or halide, at a temperature range of between about 25° C. and about 75° C. for an incubation time of between about 15 minutes and about 24 hours, to give a compound of formula II.

Another embodiment of this invention is any of the above processes having the further limitation that Step (b) is carried out in the presence of about 1 mole% of catalyst $Pd(OAc)_2$, about 2 mole % of Pd stabilizer $PPh_3$, and about 2 mole % of catalyst CuI, in base n-$BuNH_2$ and in solvent THF, at a temperature of about 35° C. for a period of about 48 hours.

Another embodiment of the process relating to the trimethylsilyl protecting group, is a process with the further limitation that in Step (d), the product of Step (c) is mixed with about 5 mole % CuI, suspended in EtOH-$Et_3N$ (7:3, v/v) and heated to about 72° C. for about 27 hours; and in Step (e) the strong base is $K_2CO_3$, and the reaction was carried out at about 65° C. for about 3.5 hours.

One preferred embodiment of the present invention is the process for synthesizing the furanyl pyridine ethyl ester of the formula

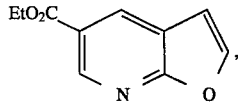

said process comprising the steps of (a) providing one equivalent of the 2-hydroxy pyridine of the formula

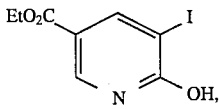

(b) reacting the pyridine of step (a) with about 1.1 to about 1.5 equivalents of the acetylene

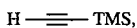

in the presence of about 1 mole % $Pd^{II}$, about 2 mole % $Cu^I$, and about 2 mole % $PPh_3$, in about 2 equivalents of n-$BuNH_2$ in THF, at a temperature of between about 35° C. and about 39° C., for a period of between about 16 hr and about 27 hr, to give a silylacetylene intermediate;

(c) reacting the resulting intermediate with about 5 mole % $Cu^I$ in EtOH-$Et_3N$ (7:3, v/v) at about 70° C. for about 27 hr; and (d) treating the product of step (c) with $K_2CO_3$, (e) to give the desired furanyl pyridine ethyl ester.

Another preferred embodiment of the present invention is the process for synthesizing the furanyl pyridine ethyl ester of the formula

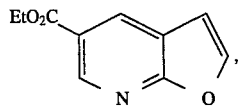

said process comprising the steps of (a) providing one equivalent of the 2-hydroxy pyridine of the formula

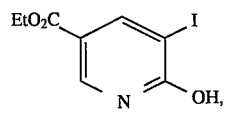

(b) reacting the pyridine of step (a) with about 1.1 to about 1.5 equivalents of the acetylene

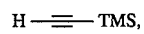

in the presence of about 1 mole % $Pd^{II}$, about 2 mole % $Cu^I$, and about 2 mole % $PPh_3$, in about 2 equivalents of n-$BuNH_2$ in THF, at a temperature of between about 35° C. and about 39° C., for a period of between about 16 hr and about 27 hr, to give a silylacetylene intermediate;

(c) reacting the resulting intermediate with an excess of one equivalent of toluenesulfonic acid in THF at about 60° C. and for about 24 hr; and (d) treating the product of step (c) with $K_2CO_3$, (e) to give the desired furanyl pyridine ethyl ester.

The processes of the present invention are schematically set forth below:

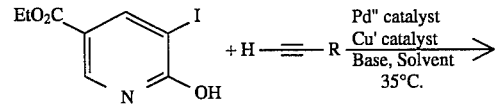

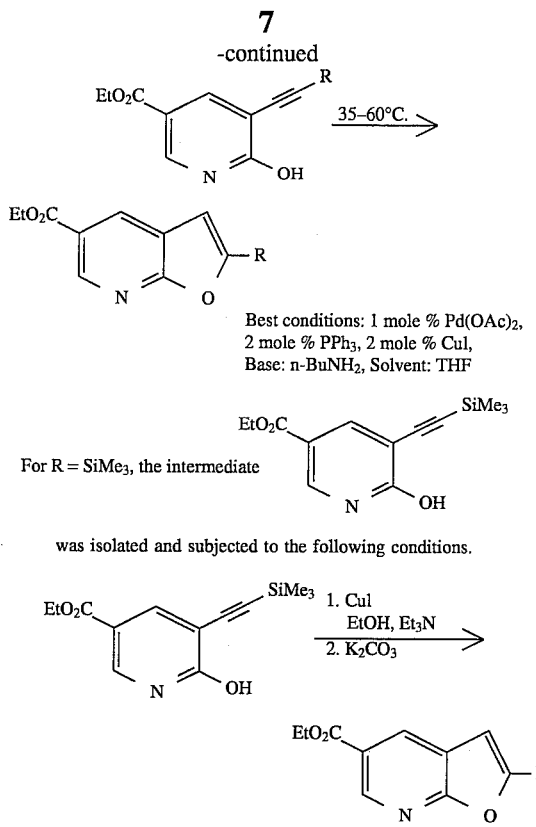

Best conditions: 1 mole % Pd(OAc)$_2$,
2 mole % PPh$_3$, 2 mole % CuI,
Base: n-BuNH$_2$, Solvent: THF For R = SiMe$_3$, the intermediate was isolated and subjected to the following conditions.

The first reaction in the present process is the coupling of substituted acetylene with substituted 2-hydroxy pyridine, in the presence of one or more catalysts. An excess of substituted acetylene is mixed with the substituted 2-hydroxy pyridine, preferably about 1.1 to about 1.5 equivalents of substituted acetylene for each equivalent of 2-hydroxypyridine. Catalysts are selected from Cu$^I$, Cu$^{II}$, Pd$^0$, Pd$^{II}$, Pt$^0$, Pt$^{II}$, Ni$^0$, or Ni$^{II}$. Preferred catalysts include Cu$^I$ and Pd$^{II}$. Most preferred is the combination of about 2 mole % Cu$^I$ and about 1 mole % Pd$^{II}$.

In the first reaction involving coupling of substituted acetylene with substituted 2-hydroxy pyridine, it is preferable to add a catalyst stabilizer, such as the palladium stabilizer PPh$_3$. Other suitable compounds having effects like a catalyst stabilizer include, but are not limited to,- trialkylphosphines, phosphites, bridged bis phosphines, acetonitrile, dibenzilidine acetone, or bis pyridyl ligands.

Additional reaction conditions for the first reaction include base and solvent at a temperature range of between about 25° C. and about 60° C., and an incubation period between about 30 minutes and about 48 hours. Bases include, but are not limited to, n-BuNH$_2$, TEA, t-BuNH$_2$, DIEA, and K$_2$CO$_3$, and are added in excess of one equivalent. Preferably, about 2.0 equivalents of n-BuNH$_2$ is used in the first reaction. Suitable solvents include any ethereal solvent, such as THF, DME or Et$_2$O, preferably THF, as well as other solvents such as DMF, N,N-dimethylacetamide, and N-methyl pyrrolidinone. Applicants have found that maximization of yield is achieved by pairing appropriate base and solvent. For example, the preferred pair is n-BuNH$_2$ and THF.

The product of the first step, a 2-hydroxy-pyridine substituted at the 5 position with an acetylene, e.g.,

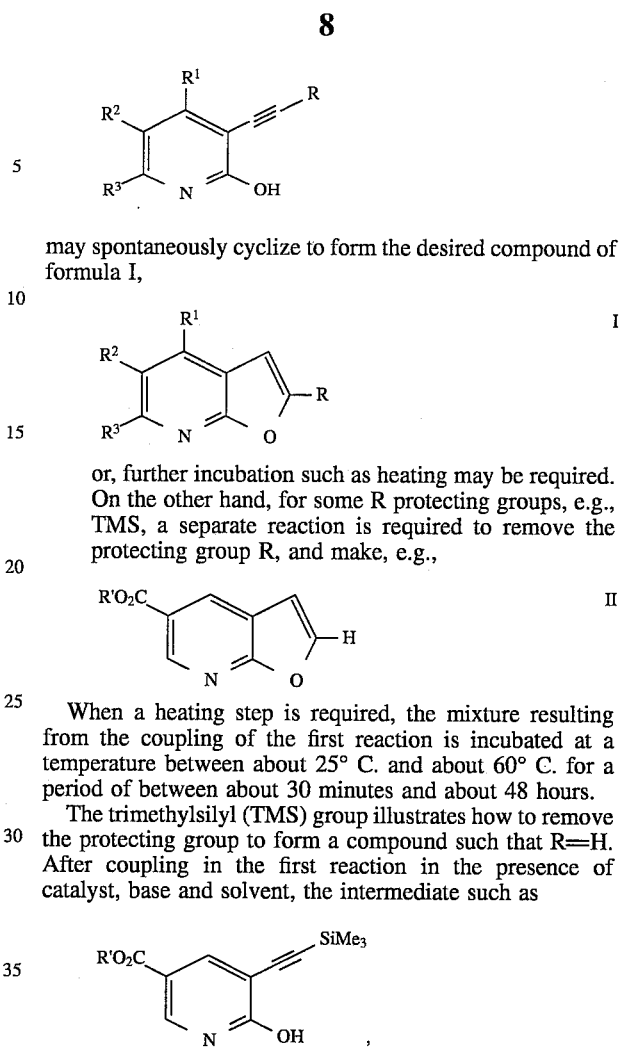

may spontaneously cyclize to form the desired compound of formula I, or, further incubation such as heating may be required. On the other hand, for some R protecting groups, e.g., TMS, a separate reaction is required to remove the protecting group R, and make, e.g., When a heating step is required, the mixture resulting from the coupling of the first reaction is incubated at a temperature between about 25° C. and about 60° C. for a period of between about 30 minutes and about 48 hours.

The trimethylsilyl (TMS) group illustrates how to remove the protecting group to form a compound such that R=H. After coupling in the first reaction in the presence of catalyst, base and solvent, the intermediate such as

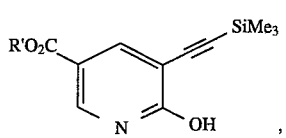

is formed. Spontaneous cyclization is substantially incomplete. To cyclize, a second reaction is performed, which is either (I) reacting with an acid which involves reacting the above intermediate with an organic acid or mineral acid in ethereal solvent or in alcoholic solvent, at a temperature between about 25° C. and about 75° C. for an incubation time of between about 30 minutes and about 48 hours; or (II) reacting with a catalyst which involves reacting the above intermediate with a catalyst selected from Cu$^I$, Cu$^{II}$ or Pd$^{II}$ in ethereal solvent or in alcoholic solvent, at a temperature between about 25° C. and about 75° C. for an incubation time of between about 30 minutes and about 48 hours.

Reaction with an acid to cyclize according to (I) is carded out with suitable organic acids or mineral acids, which include, but are not limited to CH$_3$SO$_3$H, R$_x$SO$_3$H (R$_x$ is C$_{1-6}$alkyl, aryl, camphor, chloride, fluoride, or CF$_3$), CF$_3$CO$_2$H, HCL, or H$_2$SO$_4$. Suitable ethereal solvents include, but are not limited to THF, DME or Et$_2$O. Suitable alcoholic solvents include but are not limited to MeOH, EtOH, or PrOH. The preferred acid is toluenesulfonic acid, added as an excess of one equivalent of the intermediate adduct. The preferred solvent is THF. The preferred temperature is 60° C. and the preferred incubation time is about 24 hours.

Reaction with an catalyst instead of an acid according to (II) is carded out with a suitable catalyst selected from Cu$^I$, Cu<sup>II</sup> or Pd<sup>II</sup>. A preferred catalyst is Cu<sup>I</sup>, specifically about 5 mole % of CuI in EtOH-Et<sub>3</sub>N,. Suitable ethereal solvents include, but are not limited to THF, DME or Et<sub>2</sub>O. Suitable alcoholic solvents include but are not limited to MeOH, EtOH, or PrOH. The preferred solvent is EtOH-Et<sub>3</sub>N (7:3, v/v). The preferred temperature is 70° C. and the preferred incubation time is about 24 hours.

In a third reaction, in order to form the desired compound, e.g.,

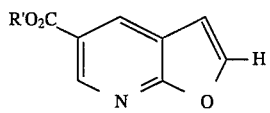

II the product of the second reaction is further treated with strong base or halide.

In the third reaction, the protecting group R is removed by treatment with a strong base or with halide. For TMS, desilylation is accomplished by treatment with metal hydroxides, alkoxide bases such as NaOMe, KO-t-Bu, KOEt and the like. Alternatively, halides desilylate, e.g., fluoride, chloride, and the like.

The processes and intermediates of this invention are useful for the preparation of end-product compounds that are useful in the inhibition of HIV protease, the prevention or treatment of infection by the human immunodeficiency virus (HIV), and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds, including their use as controls. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

HIV protease inhibitor compounds that can be made from the intermediates and processes of the instant invention are disclosed in EPO 541,164. The HIV protease inhibitory compounds may be administered to patients in need of such treatment in pharmaceutical compositions comprising a pharmaceutical carder and therapeutically-effective amounts of the compound or a pharmaceutically acceptable salt thereof. EPO 541,164 discloses suitable pharmaceutical formulations, administration routes, salt forms and dosages for the compounds.

The compounds of the present invention, may have asymmetric centers and occur as racemates, racemic mixtures and as individual diastereomers, or enantiomers with all isomeric forms being included in the present invention.

When any variable (e.g., aryl) occurs more than one time in any constituent, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl; t-Bu is tert-butyl); As used herein, "aryl" is intended to mean phenyl (Ph) or naphthyl. Halo is s iodo, bromo or chloro. It is understood that any 2-pyridone is equivalent to its corresponding 2-hydroxy pyridine.

The term heterocycle or heterocyclic, as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiopyranyl, tetrahydrofuryl, tetrahydropyranyl, and tetrahydrothienyl, thienyl, benzothienyl, thiamorpholinyl, thiamorpholinyl sulfoxide, thiamorpholinyl sulfone and isobenzothiopyranyl.

Representative experimental procedures utilizing the novel process are detailed below. These procedures are exemplary only and are not limitations on the novel process of this invention.

EXAMPLE 1

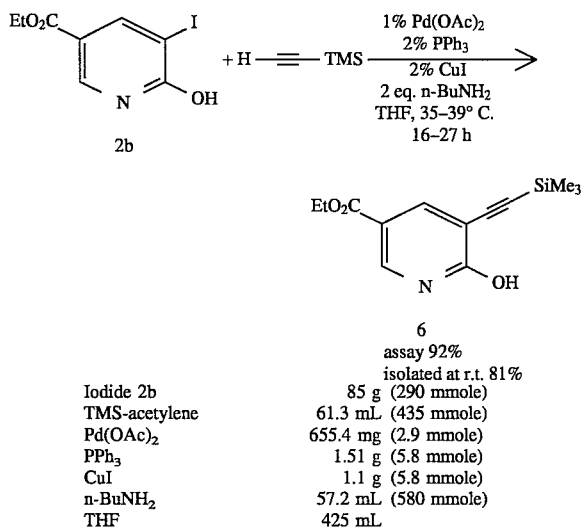

| | |
|---|---|
| Iodide 2b | 85 g (290 mmole) |
| TMS-acetylene | 61.3 mL (435 mmole) |
| Pd(OAc)<sub>2</sub> | 655.4 mg (2.9 mmole) |
| PPh<sub>3</sub> | 1.51 g (5.8 mmole) |
| CuI | 1.1 g (5.8 mmole) |
| n-BuNH<sub>2</sub> | 57.2 mL (580 mmole) |
| THF | 425 mL |

The iodide, Pd(OAc)<sub>2</sub>, PPh<sub>3</sub> and CuI were added to a 3-neck round bottom flask under N<sub>2</sub> followed by THF (425 mL) and the TMS-acetylene. This initial slurry was treated with n-BuNH<sub>2</sub> and the resulting homogeneous green solution was heated to 35° C.–39° C. (bath temperature).

Although the present procedure was performed using 1.5 equiv of TMS-acetylene, only 1.1 equiv of reagent is required as demonstrated on a 3 g reaction. The THF and n-BuNH$_2$ were dried over 4A molecular sieves but no degassing is needed.

After ca. 1 hr of heating the green color turned yellow with complete consumption of starting material occurring after 16 hours at that temperature [assay:50:50 ACN-H$_2$O (0.1% H$_3$PO$_4$) shows 92% yield based on standard].

The volatiles were concentrated in vacuo at 35° C. and the residue was dissolved in EtOAc (500 mL) and washed in sequence with disodium EDTA (2×250 mL concentration), 10% aqueous NaHSO$_3$ (250 mL), 0.1N HCl (250 mL) and saturated aqueous NaHCO$_3$ (250 mL). The organic layer was dried over MgSO$_4$ and concentrated in vacuo. The residual solid was suspended in 510 mL of 10:1 hexane-EtOAc and the slurry heated to 70° C. (bath temp) for 15 min and then cooled to 25° C. where it was stirred for 2 h. It was then filtered and the cake was washed with 360 mL of 10:1 hexane-EtOAc at ambient temperature. The solid was dried in vacuo at 40° C. to give 61.8 g of 6 (81%).

EXAMPLE 2

Preparation of N-(2(R)-hydroxy-1(S)-indanyl)-2(R)-phenylmethyl-4 (S)-hydroxy-5-(1-(4-(3-furo[2,3]-pyridylmethyl)-2(S)-N'-(t-butylcarboxamido)piperazinyl)-pentaneamide

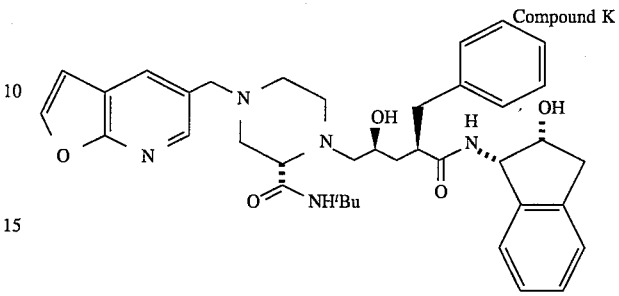

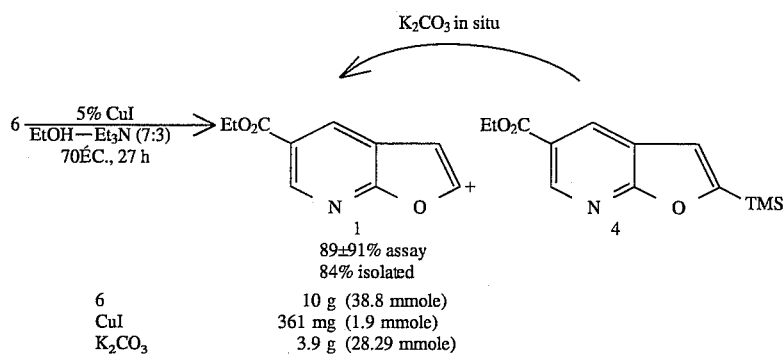

The silylacetylene 6 and CuI were suspended in EtOH (76 mL) and treated with Et$_3$N (32 mL) to give a greenish homogeneous solution which was heated to 72° C. for 27 h. When the reaction was judged complete by LC milled K$_2$CO$_3$ was added and the mixture heated to 65° C. for 3.5 h.

The reaction was monitored by LC [50:50 ACN-H$_2$O (0.1% H$_3$PO$_4$)] with the following compounds present: 6, the desilylated starting material 8, 1 and 4. Proceed further if 6<0.4 A% and 8<1 A%. [assay yield 87%]. The mixture was filtered through the cake, washed with toluene and the combined filtrate concentrated in vacuo. Toluene (300 mL) was added and the brownish solution was washed with 1N HCl (200 mL) followed by 2N HCl (100 mL). The color of the organic was now pale yellow; it was then Washed with sat. aqueous bicarbonate and then concentrated in vacuo. The crude yellow solid (6.01 g, 84%) was >99.3 wt % pure.

LC CONDITIONS
50:50 ACN-H$_2$O (0.1% H$_3$PO$_4$), λ=210 nm, 1.5 mL/min., Zorbax Rx-C8

| | |
|---|---|
| 1 | 4.5 min. |
| 2b | 2.7 min |
| 4 | 19.8 min. |
| 5 | 2.13 min. |
| 6 | 6.3 min. |
| 7 | 2.3 min. |
| 8 | 2.3 min. |

To a solution of N-(2(R)-hydroxy-1 (S)-indanyl)-2(R)-phenylmethyl-4 (S)-hydroxy-5(-2(S)-N'-(t-butylcarboxamido)piperazinyl))pentaneamide (6.50 g, 12.48 mmol) dissolved in 12 mL of dimethylformamide, under argon, was added 3-chloromethylfuro-[2,3-b]pyridine hydrochloride (2.80 g, 13.72 mmol) and triethylamine (5.21 mL, 37.44 mmol). After 18 h the reaction mixture was diluted with 400 mL of ethyl acetate and washed with sat'd NaHCO$_3$ (1×25 mL), water (5×20 mL), and brine (1×25 mL). The solution was dried over MgSO$_4$, filtered and concentrated to an oil. The residue was purified via flash column chromatography (60×150 mm column, gradient elution CH$_2$Cl$_2$.CH$_2$Cl$_2$ sat'd with NH$_3$: MeOH 60:39:1.0 (1000 mL), 60:38:2 (1500 mL), 60:37:3 (1500 mL), 60:36:4 (1500 mL). Titrated the resulting foam in ethyl acetate and the desired product was filtered and dried overnight under high vacuum at 65° C. to provide 5.30 g of white crystalline solid. Mixed fractions from the column chromatography could be combined and repurified to afford more product. mp 183.5°–184.5° C. $^1$H NMR (400 MHz, CDCl$_3$) δ 8.25 (d, J=2.2 Hz, 1H), 7.85 (d, J=2.0 Hz, 1H), 7.75 (s, 1H), 7.73 (d, J=2.4 Hz, 1H), 7.32–7.10 (m, 9H), 6.75 (d, J=2.4 Hz, 1H), 5.95 (d, J=8.6 Hz, 1H), 5.27 (dd, J=8.5, and 4.8 Hz, 1H), 4.27–4.26 (m, 1H), 4.12 (br s, 1H), 3.89–3.83 (m, 1H), 3.51 (s, 2H), 3.29 (dd, J=17.5 and 4.0 Hz, 1H), 3.16 (dd, J=3.66 and 3.48 Hz, 1H), 3.15 (dd, J=6.6 and 5.1 Hz, 1H), 2.94–2.50 (m, 11H), 2.36–2.34 (m, 1H), 1.66 (s, 1H), 1.62–1.47 (m, 1H), 1.35 (s, 9H).

Analysis calculated for C$_{38}$H$_{47}$N$_5$O$_5$ C, 69.81; H, 7.25; N, 10.71 Found: C., 69.46; H, 7.22; N, 10.69

EXAMPLE 3

Preparation of Furo[2,3-b]pyridin-5-carboxylic acid

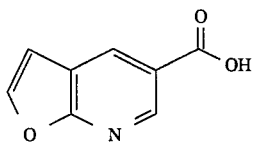

To a suspension of furo[2,3-b]pyridine-2,5-dicarboxylic acid (0.36 g, 1.484 mmol) in 3 mL of quinoline, under Ar, was added Cu powder (180 mg, 2.82 mmol) and warmed to 210° C. for 1.5 h. The reaction was cooled to RT and diluted with 50 mL of methylene chloride and filtered through celite. The organic layer was extracted with sat'd $NaCO_3$ (2×40 mL), acidified to pH 3 with 3N HCl, and filtered to afford 80 mg of a tan solid. The aqueous layer was extracted with ether/methanol (85/15) (3×50 mL) and washed with brine (1×10 mL), dried over $MgSO_4$, filtered and concentrated to afford an additional 35 mg of product. $^1H$ NMR (400 MHz, $CD_3OD$) δ8.89 (s, 1H), 8.67 (d, J=2.0 Hz, 1H), 7.97 (d, J=2.5 Hz, 1H), 7.01 (d, J=2.4 Hz, 1H).

EXAMPLE 4

Preparation of methyl furo[2,3-b]pyridine-5-carboxylate

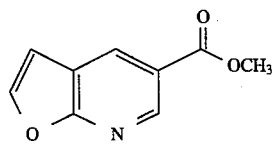

To furo[2,3-b]pyridine-5-carboxylic acid (3.0 g, 18.40 mmol) dissolved in 40 mL of methanol was added 160 mL of chloroform and then trimethysilyldiazomethane (42 mL, 10% solution in hexanes) slowly. After 0.5 h 4 drops glacial acetic acid was added and the reaction mixture was concentrated. This provided 3.20 g as an off white solid. $^1H$ NMR (400 MHz, $CDCl_3$) δ9.02 (d, J=2.0 Hz, 1H), 8.60 (d, J=2.0 Hz, 1H), 7.79 (d, J=2.5 Hz, 1H), 6.87 (d, J=2.5 Hz, 1H), 3.98 (s, 3H).

EXAMPLE 5

Preparation of 5-hydroxymethyl furo[2.3-b]pyridine

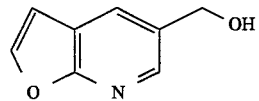

A flame dried 500 mL round bottom flask was charged with methyl furo[2,3-b]pyridine-5-carboxylate (3.20 g, 18.08 mmol) dissolved in 90 mL of THF and cooled to 0° C. To this was added diisobutylaluminum hydride (46 mL, 46.1 mmol, 1M solution in hexanes) over 10 minutes and the cooling bath removed. After 4 h the reaction mixture was cooled to 0° C. and slowly quenched with rochelle salts (100 mL). After an additional 18 h the layers were separated and the aqueous layer was extracted with ethyl acetate (4×40 mL). The combined organic layers were washed with brine (1×20 mL), dried over $MgSO_4$, filtered and concentrated. The residue was purified via flash column chromatography (40×150 mm column, gradient elution $CH_2Cl_2:CH_2Cl_2$ sat'd with $NH_3$: MeOH 60:39:1.0 (1000 mL), 60:38:2 (1000 mL), 60:37:3 (1000 mL), 60:36:4 (1000 mL). This provided 2.16 g of a white solid.

$^1HNMR$ (400 MHz, $CDCl_3$) δ8.19 (d, J=2.0 Hz, 1H), 7;92 (d, J=2.0 Hz, 1H), 7.64 (d, J=2.5 Hz, 1H). 6.69 (d, J=2.4 Hz, 1H), 4.78 (d, J=3.8 Hz, 2H), 4.69 (br s, 1H).

EXAMPLE 6

Preparation of 3-chloromethyl furo[2,3-b]pyridine hydrochloride

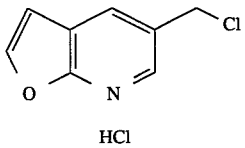

To a solution of 5-hydroxymethyl furo[2,3-b]pyridine dissolved in 9 mL of methylene chloride cooled to 0° C. was added thionyl chloride (4.23 mL, 57.99 mmol). The ice bath was removed and after 1 h the reaction mixture was concentrated to afford 2.86 g of an off white solid. $^1H$ NMR (400 MHz, $CDCl_3$) δ8.40 (d, J=2.0 Hz, 1H), 8.13 (d, J=2.2 Hz, 1H), 7.80 (d, J=2.4 Hz, 1H), 6.86 (d, J=2.4 Hz, 1H), 4.74 (s, 2H).

EXAMPLE 7

Preparation of Amide 9

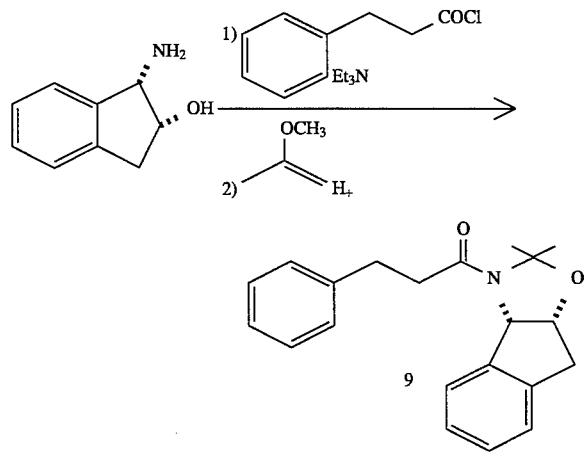

A solution of (−)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature between 14°–24° C. with an ice-water cooling batch. After addition, the mixture was aged at 18 to 20° C. for 30 minutes and checked by HPLC analysis for the disappearance of (−)-cis-1-aminoindan-2-ol.

Progress of the reaction is monitored by high performance liquid chromatography (HPLC) analysis: 25 cm Dupont C8-RX column, 60:40 acetonitrile/10 mM ($KH_2PO_4$/ $K_2HPO_4$), 1.0 mL/min., injection volume=20 mL, detection=200 nm, sample preparation=500×dilution. Approximate retention times:

| retention time (min.) | identity |
|---|---|
| 6.3 | cis-aminoindanol |

The reaction was treated with pyridinium p-toluenesulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous $NaHCO_3$ (10 L). The mixture was agitated and the layers were separated. The ethyl acetate extract was washed with 5% aqueous $NaHCO_3$ (10 L) and water (4 L). The ethyl acetate extract was dried by atmospheric distillation and solvent switched to cyclohexane (total volume of ~30 L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 9 (86.4%, 98 area % by HPLC). $^1H$ NMR (300.13 MHz, $CDCl_3$, major rotamer) $\delta$ 7.36–7.14 (m, 9 H), 5.03 (d, J=4.4, 1 H), 4.66 (m, 1 H), 3.15 (m, 2 H), 3.06 (br s, 2 H), 2.97 (m, 2 H), 1.62 (s, 3 H), 1.37 (s, 3 H); $^{13}C$ NMR (75.5 MHz, $CDCl_3$, major rotamer) $\delta_c$ 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1.

Anal. Calcd for $C_{21}H_{23}NO_2$: C, 78.47; H, 7.21; N, 4.36. Found: C, 78.65; H, 7.24; N, 4.40.

EXAMPLE 8

Preparation of Epoxide 11 Tosylate Method

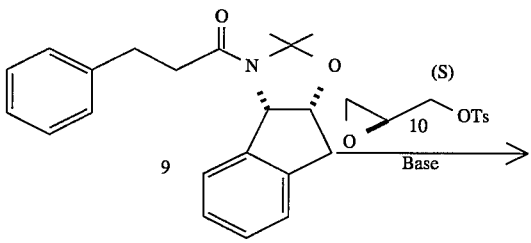

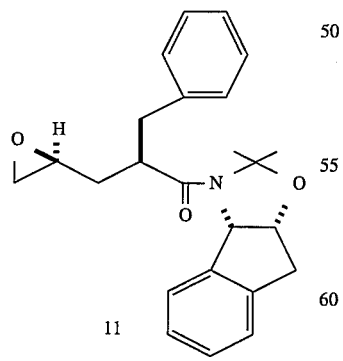

A solution of acetonide 9 (1000 g, 3.11 mol) and 2(S)-glycidyl tosylate 10 (853 g, 3.74 mol, 1.2 equiv.) in 15.6 L of THF (KF =22 mg/mL) in a 50 L 4-neck round bottom flask, equipped with a thermocouple, mechanical stirrer, addition funnel and nitrogen inlet adapter was degassed 3 times via vacuum-nitrogen purge and cooled to −56° C. Then, lithium hexamethyldisilazide ($LiN[(CH_3)_3Si]_2$)(2.6 L, 1.38 M, 1.15 equiv.) was added over 2 h, while keeping the internal temperature between −50 to −45° C. The reaction mixture was stirred at −45 ° to −40° C. for 1 h and then allowed to warm to −25° C. over 1 h. The mixture is stirred between −25° to −22° C. for 4 h (or until the starting acetonide is 3.0 area %).

Progress of the reaction is monitored by HPLC analysis: 25 cm×4.6 nm Zorbax Silica column, 20% ethyl acetate in hexane, 2.0 mL/min, injection volume=20 mL, detection= 254 nm, sample preparation=100×dilution. Approximate retention times:

| retention time (min.) | identity |
|---|---|
| 5.5 | amide 9 |
| 6.5 | glycidyl tosylate 10 |
| 13.5 | epoxide 11 |

The reaction mixture was quenched with DI water (6.7 L) at −15° C. and partitioned with ethyl acetate (10 L). The mixture was agitated and the layers were separated. The ethyl acetate extract was washed with a mixture of 1% aqueous $NaHCO_3$ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 11 (61.2%, 98.7 area % of the major epoxide by HPLC). $^{13}C$ NMR (300 MHz, $CDCl_3$) $\delta$ 171.1, 140.6, 140.5, 139.6, 129.6, 128.8, 128.2, 127.2, 126.8, 125.6, 124.1, 96.8, 79.2, 65.8, 50.0, 48.0, 44.8, 39.2, 37.4, 36.2, 26.6, 24.1.

EXAMPLE 9

Preparation of penultimate 14

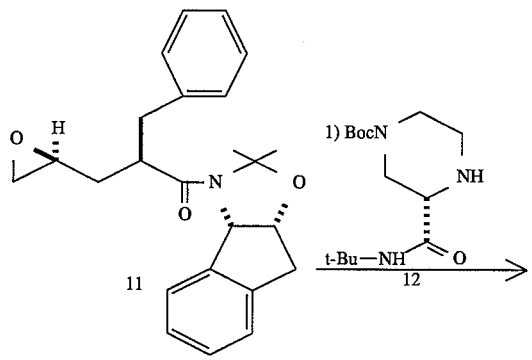

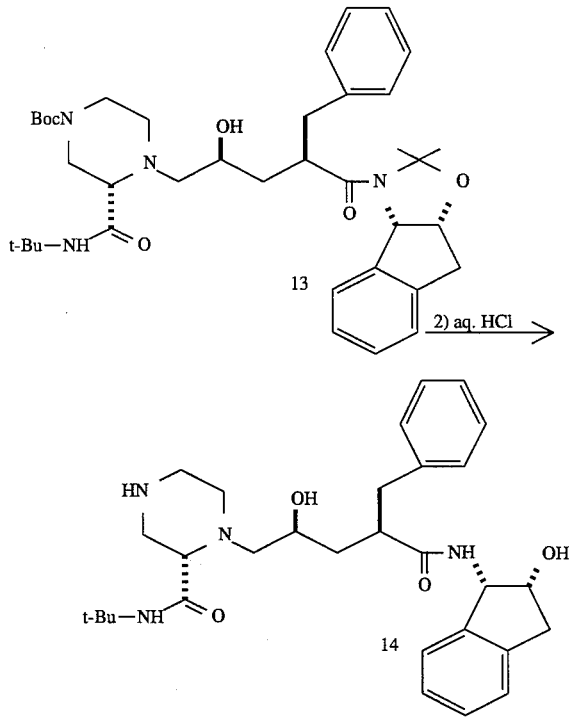

| retention time (min) | identity |
| --- | --- |
| 11.9 | penultimate 14 |
| 15.1 | coupled product 13 |

The mixture was cooled to 0° C. and 7.5 L of 50% NaOH was slowly added to adjust the pH of the mixture to pH=11.6, while keeping the temperature less than 25° C. during the addition. The mixture was partitioned with ethyl acetate (40 L) and water (3 L). The mixture was agitated and the layers were separated. The organic phase (60 L) was concentrated under reduced pressure (29" of Hg) and solvent switched to DMF and concentrated to a final volume of 10.5 L (KF=1.8 mg/mL). The HPLC assay yield of 14 in ethyl acetate was 86.5%. The penultimate compound 14 in DMF was directly used in the next step without further purification. For isolated 14: $^{13}$C NMR (75.4 MHz, CDCl$_3$) δ175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 10

Preparation of monohydrate of Compound J

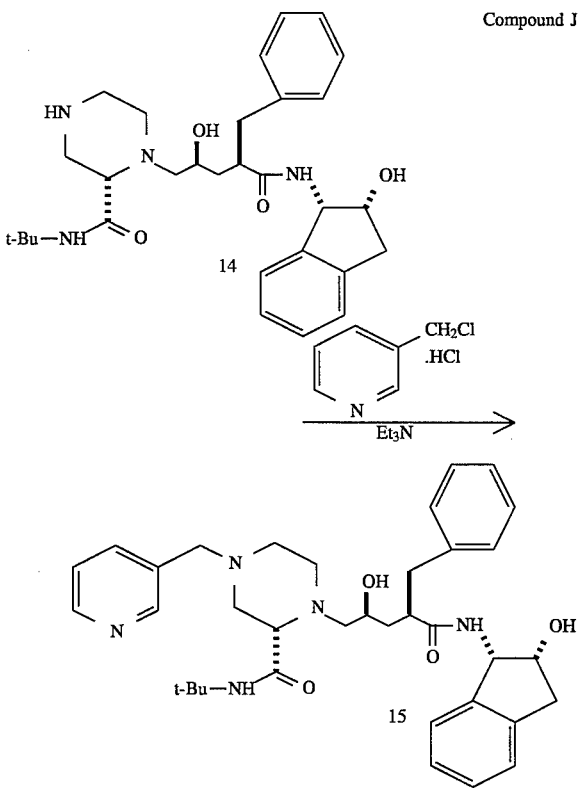

A slurry of the 2(S)-t-butylcarboxamide-4-N-Boc-piperazine 12 (1950 g, 6.83 mol, >99.5% ee) (ee=enantiomeric excess) and the epoxide 11 (2456 g, 97.5:2.5 mixture of 4 S/R epoxides, 6.51 mol) in isopropanol (2-propanol, 18.6 L) in a 72 L round bottom flask with four inlets, equipped with a mechanical stirrer, reflux condenser, steam bath, Teflon coated thermocouple and nitrogen inlet, was heated to reflux (internal temperature was 84°–85° C). After 40 min, a homogeneous solution was obtained. The mixture was heated at reflux for 28 h.

The internal temperature during reflux was 84°–85° C. Progress of the reaction was monitored by HPLC analysis: 25 cm Dupont C8-RX column, 60:40 acetonitrile/10 mM (KH$_2$PO$_4$/K$_2$HPO$_4$), 1.0 mL/min., detection=220 nm, sample preparation=2 μL, reaction mixture diluted to 1 mL in acetonitrile. Approximate retention times:

| retention time (min) | identity |
| --- | --- |
| 4.8 | piperazine 12 |
| 8.9 | epoxide 11 |
| 15.2 | coupled product 13 |

After 28 h, the remaining epoxide 11 and coupled product 13 (by HPLC analysis) were 1.5 area % and 91–93 area %, respectively. The mixture was cooled to 0° to 5° C. and 20.9 L of 6 N HCl was added while keeping the temperature below 15° C. After the addition was complete, the mixture was warmed to 22° C. Evolution of gas is noted at this point (isobutylene). The mixture was aged at 20° to 22° C. for 6 h.

Progress of the reaction was monitored by HPLC analysis: same conditions as above. Approximate retention times:

| retention time (min) | identity |
| --- | --- |
| 7.0 | cis-aminoindanol |

The solution of 14 in DMF (10.5 L, KF=10 mg/mL) from the previous step was charged with 8 L of sieve dried DMF (KF. <30 mg/L) and the mixture was heated with a steam bath under vacuum of 30" of Hg to distill off mainly water and/or any residual isopropanol or ethyl acetate solvent. The final concentrate volume was 13.5 L (KF=1.8 mg/mL) and then triethylamine (2.86 L, 20.51 mol) was added to the 25° C. solution followed by 3-picolyl chloride hydrochloride (96%, 1287 g, 7.84 mol). The resulting slurry was heated to 68° C.

The progress of the reaction was followed by HPLC analysis using the same conditions as the previous step. Approximate retention times:

| Retention time (min) | Identity |
|---|---|
| 2.7 | DMF |
| 4.2 | 3-picolyl chloride |
| 4.8 | Compound J |
| 9.1 | penultimate 14 |

The mixture was aged at 68° C. until the residual penultimate compound 14 was <0.3 area % by HPLC analysis.

The mixture was stirred at 68° C. for 4 h, then cooled to 25° C. and partitioned with ethyl acetate (80 L) and a mixture of 24 L of saturated aqueous NaHCO₃ and distilled water (14 L). The mixture was agitated at 55° C. and the layers were separated. The ethyl acetate layer was washed three times with water (20 L) at 55° C. The washed ethyl acetate layer is concentrated at atmospheric pressure to a final pot volume of 30 L. At the end of the atmospheric concentration, water (560 mL) was added to the hot solution and the mixture was cooled to 55° C. and seeded with Compound J monohydrate. The mixture was cooled to 4° C. and filtered to collect the product. The product was washed with cold ethyl acetate (2×3 L), and dried at house vacuum at 25° C. to afford 2905 g (70.7%) of Compound J monohydrate as a white solid.

EXAMPLE 11

Pyrazine-2-tert-butyl carboxamide 17

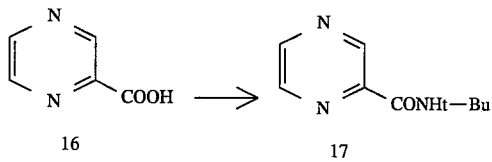

| 2-Pyrazinecarboxylic acid (8) | 3.35 kg (27 mol) |
| Oxalyl chloride | 3.46 kg (27.2 mol) |
| tert-butylamine (KF = 460 μg/ml) | 9.36 L (89 mol) |
| EtOAc (KF = 56 μg/ml) | 27 L |
| DMF | 120 mL |
| 1-Propanol | 30 L |

The carboxylic acid 16 was suspended in 27 L of EtOAc and 120 mL of DMF in a 72 L 3-neck flask with mechanical stirring under N₂ and the suspension was cooled to 2° C. The oxalyl chloride was added, maintaining the temperature between 5° and 8° C.

The addition was completed in 5h. During the exothermic addition CO and CO₂ were evolved. The HCl that was formed remained largely in solution. A precipitate was present which is s probably the HCL salt of the pyrazine acid chloride. Assay of the acid chloride formation was carried out by quenching an anhydrous sample of the reaction with t-butylamine. At completion <0.7% of acid 16 remained.

The assay for completion of the acid chloride formation is important because incomplete reaction leads to formation of a bis-tertbutyl oxamide impurity.

The reaction can be monitored by HPLC: 25 cm Dupont Zorbax RXC8 column with 1 mL/min flow and detection at 250 nm; linear gradient from 98% of 0.1% aqueous H₃PO₄ and 2% CH₃CN to 50% aqueous H₃PO₄ and 50% CH₃CN at 30 min. Retention times: acid 16=10.7 min, amide 17=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated ten-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% NaHCO₃ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 17 was concentrated at 10 mbar to 25% of the original volume. 30 L of 1-propanol were added, and the distillation was continued until a final volume of 20 L was reached.

At this point, the EtOAc was below the limit of detection in the ¹H NMR (<1%). The internal temperature in this solvent change was <30° C. A 1-propanol/EtOAC solution of 3 was stable to reflux at atmospheric pressure for several days. Evaporation of an aliquot gave a tan solid m.p 87°–88° C. ¹³C NMR (75 MHz, CDCl₃, ppm) 161.8, 146.8, 145.0, 143.8, 142.1, 51.0, 28.5.

EXAMPLE 12 rac-2-tert-Butyl-carboxamide-piperazine 18

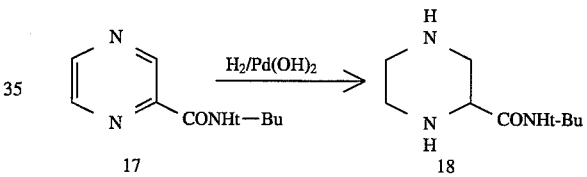

Materials

Pyrazine-2-tert-butylcarboxamide 17 2.4 kg (13.4 mol) in 1-Propanol solution 12L 20% Pd(OH)₂/C 16 wt. % water 144 g.

The pyrazine-2-tert-butylcarboxamide 17/1-propanol solution was placed into the 5 gal autoclave. The catalyst was added and the mixture was hydrogenated at 65° C. at 40 psi (3 atm) of H₂.

After 24 h. the reaction had taken up the theoretical amount of hydrogen and GC indicated <1% of 17. The mixture was cooled, purged with N₂ and the catalyst was removed by filtration through Solka Floc. The catalyst was washed with 2 L of warm 1-propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C./min to 250° C., retention times: 17=7.0 min, 18=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 18 is 133g/L.

Evaporation of an aliquot gave 18 as a whim solid m.p. 150°–151° C.; ¹³C NMR (75 MHz, D₂O, ppm) 173.5, 59.8, 52.0, 48.7, 45.0, 44.8, 28.7.

EXAMPLE 13

(S)-2-tert-Butyl-carboxamide-piperazine bis (S)-Camphorsulfonic acid salt (S)-19

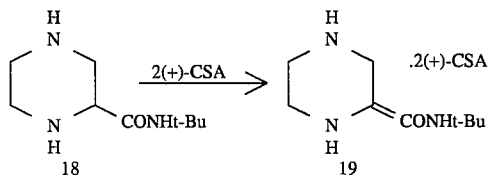

| Materials | |
|---|---|
| rac-2-tert-Butyl-carboxamide-piperazine 18 in 1-Propanol Solution | 4.10 kg (22.12 mol) in 25.5 Kg solvent |
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 18 in 1-propanol was charged to a 100 L flask with an attached batch concentrator. The solution was concentrated at 10 mbar and a temperature <25° C. to a volume of ca 12 L.

At this point the product had precipitated from the solution, but went back into a solution when the mixture was heated to 50° C.

Analysis of a homogeneous aliquot indicated that the concentration of 18 was 341 g/L. The concentration was determined by HPLC: 25 cm Dupont Zorbax RXC8 column with 1.5 mL/min flow and detection at 210 nm, isocratic (98/2) $CH_3CN/0.1\%$ aqueous $H_3PO_4$. Retention time of 18:2.5 min.

Acetonitrile (39 L) and water (2.4 L) were added to give a clear, slightly brown solution.

Determination of the water content by KF titration and $CH_3CN/1$-propanol ratio by $^1H$ NMR integration showed that the $CH_3CN/1$-propanol/$H_2O$ ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21° C. over 8 h.

The product precipitated at 62° C. The product was filtered without aging at 21° C., and the filter cake was washed with 5 L of the $CH_3CN/1$-propanol/$H_2O$ 26/8/1.6 solvent mixture. It was dried at 35° C. in the vacuum oven with $N_2$ bleed to give 5.6 Kg (39%) of 19 as a white crystalline solid m.p 288°–290° C. (with decomp.) $[\alpha]D^{25}=$ 18.9° (c=0.37, $H_2O$). $^{13}C$ NMR (75 MHz, $D_2O$, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 19 (33 mg) was suspended in 4 mL of EtOH and 1 mL of $Et_3N$. $Boc_2O$ (11 mg) was added and the reaction mixture was allowed to age for 1 h. The solvent was completely removed in vacuo, and the residue was dissolved in ca. 1 mL of EtOAc and filtered through a Pasteur pipet with $SiO_2$, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 14

(S)-2-tert-Butylcarboxamide-4-tert-butoxycarbonyl-piperazine 12 from salt 19

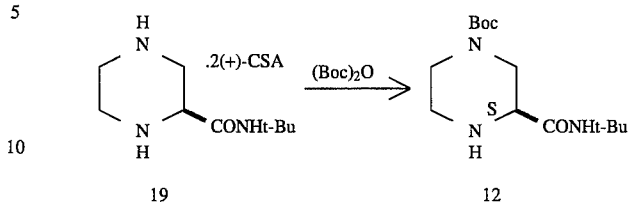

| Materials | |
|---|---|
| (S)-2-tert-Butyl-carboxamide-piperazine Bis (S)-(+)-CSA salt 19, 95% ee | 5.54 Kg (8.53 mol) |
| Di-tert-butyl dicarbonate | 1.86 Kg (8.53 mol) |
| $Et_3N$ | 5.95 L (42.6 mol) |
| EtOH Punctilious 200 proof | 55 L |
| EtOAc | 2 L |

To the (S)-CSA salt 19 in a 100 L 3-neck flask with an addition funnel under $N_2$ was added EtOH, followed by triethylamine at 25° C. The solid dissolved readily on the addition of the $Et_3N$. The $Boc_2O$ was dissolved in EtOAc and charged to the addition funnel. The solution of $Boc_2O$ in EtOAc was added at such a rate as to keep the temperature below 25° C. The addition took 3 h. The reaction mixture was aged for 1 h after completion of the addition of the $Boc_2O$ solution.

The reaction can be monitored by HPLC:25 cm Dupont Zorbax RXC8 column with 1 mL/min flow and detection at 228 nm, isocratic (50/50) $CH_3CN/0.1M$ $KH_2PO_4$ adjusted to pH=6.8 with NaOH. Retention time of 12=7.2 min. The chiral assay was carried out using the same system as in the previous step. The reaction could also be monitored by TLC with a 100% EtOAc as the solvent. ($R_f=0.7$)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous $Na_2CO_3$ solution, 2×10 L Di water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under $N_2$ bleed to give 1.87 Kg (77%, >99.9 area % by HPLC, R-isomer below level of detection) of 12 as a slightly tan powder. $[\alpha]D^{25}=22.0°$ (c=0.20, MeOH), m.p 107° C.; $^{13}C$ NMR (75 MHz, $CDCl_3$, ppm) 170.1, 154.5, 79.8, 58.7, 50.6, 46.6, 43.6, 43.4, 28.6, 28.3.

EXAMPLE 15

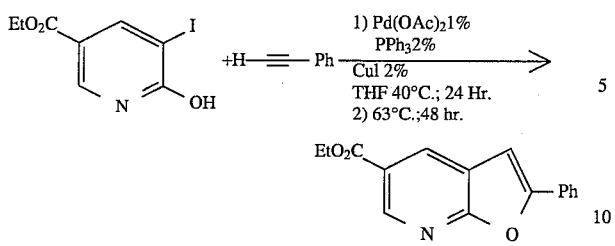

In a flame dried, 50 ml round bottom flask, iodide 2b (6.82 mmol) was added followed by Pd (OAc)$_2$ (0.0682 mmol), triphenyl-phosphine (0.137 mmol), and CuI (0.137 mmol). All solids were added in succession and, under slight N$_2$ pressure, were suspended in THF (11.0 mL). Phenylacetylene (7.64 mmol) and n-BuNH$_2$ (13.7 mmol) were added to give a green homogenous solution. The reaction mixture was then sealed under N$_2$ pressure and heated at +40° C. for 22–24 hrs where consumption of ethyl ester starting material and formation of the acetylene adduct was observed. The reaction mixture was then heated to +63° C. for 44–48 hrs where the acetylene adduct converted to the desired furopyridine. The reaction mixture was then partitioned between methylene chloride (50 ml) and disodium EDTA (5% aq. solution, 50 ml). The organic extract was then washed with sodium bisulfite (10% aq. solution, 50 mL), followed by 0.1N HCl (50 mL) and saturated aq. NaHCO$_3$ solution (50 mL). The organic extract was then dried over MgSO$_4$, filtered, and concentrated in vacuo. The crude material was then flashed chromatographed on SiO$_2$ using 12:1 hexanes-EtOAc to afford the desired product in 78% isolated yield.

EXAMPLE 16

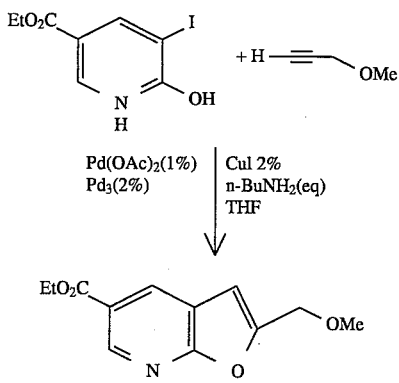

The iodide (1.76 g, 6 mmole), Pd(OAc)$_2$ (13.5 mg, 0.06 mmole), PPh$_3$ (31.5 mg, 0.1 mmole), CuI (22.9 mg, 0o12 mmole) were added as solids in a round-bottom flask under N$_2$ followed by n-BuNH$_2$ (1.2 mL, 12.0 mmole) and propanyl methyl ether (0.56 mL, 6.6 mmole) to give a green homogenous solution which was heated to 45°–50° C. for 48 hours. When HPLC analysis indicated no starting material was present, the mixture was partitioned between CH$_2$Cl$_2$ and disodium EDTA (5% aqueous solution) and the organic layer was washed in sequence with aqueous sodium bisulfite, 0.5 N HCl and NaHCO$_3$ (aq). The organic layer was dried over MgSO$_4$, filtered and concentrated in vacuo and then chromatographed (flush-grade SiO$_2$, 3:1 hexanes-EtoAc) to give 1.07 g of product (76%).

EXAMPLE 17

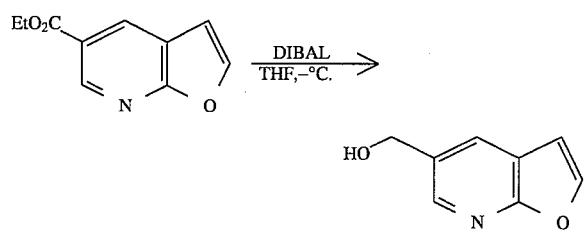

The ester (547.6 g, 2.87 mole) was dissolved in 12.9 Lt of dry THF and cooled to −7° C. and treated with 1.11 Lt of neat diisobutyl aluminum hydride (DIBAL) so that the temperature does not exceed −5° to −6° C. When tlc indicated complete consumption of starting material (ca 35 min) add saturated Na, K tartrate [10 kg of Na, K tartrat in 20 Lt of H$_2$O] so that the temperature remained below −4° C., (ca 8 Lt of "salt" solution added). Stop cooling, heat the mixture to 40° C. to ensure degassing of the mixture for 2 hours. Separate layers, add 12 Lt of isopropyl acetate and wash with additional 2 Lt of Na, K tartrate, separate layers and wash organic with 2 Lt of H$_2$O. Dry organic over MgSO$_4$, filter and recrystallize from Hexanes-1 PAC to give 780.3 g of alcohol.

EXAMPLE 18

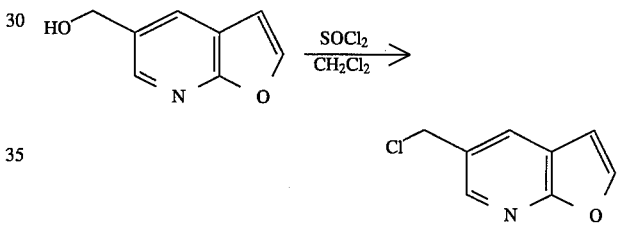

The alcohol (780 g, 4.81 mole, corrected for purity) was dissolved in 16 Lt of CH$_2$Cl$_2$ and the solution cooled to −2° C. SOCl$_2$ was added over 15 min so that the temperature did not exceed 0° C. The solution was warmed up to 15° C. for 2 hours at which point HPLC assay showed no starting material remaining. Slow addition of 16 Lt of NaHCO$_3$ (aqueous) [caution CO$_2$ evolution] produced a biphosic mixture. The organic layer was separated and treated with 40 g activated carbon (Darco G-60) and 1 kg of anhydrous Na$_2$SO$_4$, filtered and concentrated in vacuo to give 850.7 g of the desired chloride.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. The process for synthesizing a substituted furanyl pyridine of formula II:

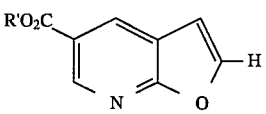

wherein

R' is C$_{1-4}$alkyl, or aryl;
comprising the steps of (a) providing one equivalent of the halogenated pyridine of the formula

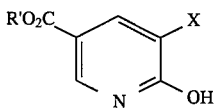

wherein X is Br, I, or Cl;

(b) reacting the halogenated pyridine of Step (a) with 1.0 or more equivalents of the acetylene

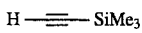

in the presence of catalyst selected from one or more of $Cu^I$, $Cu^{II}$, $Pd^0$, $Pd^{II}$, $Pt^0$, $Pt^{II}$, $Ni^0$, or $Ni^{II}$, in 1.0 or more equivalents of base and in ethereal solvent, at a temperature between about 25° C. and about 60° C., for a period of between about 30 minutes and about 48 hours;

(c) isolating the product

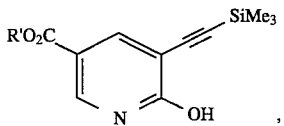

(d) reacting the product of Step (c) with an organic acid or mineral acid in ethereal solvent or in alcoholic solvent, at a temperature between about 25° C. and about 75° C. for an incubation time of between about 30 minutes and about 48 hours; and (e) treating with strong base or halide, at a temperature range of between about 25° C. and about 75° C. for an incubation time of between about 15 minutes and about 24 hours, to give a compound of formula II.

2. The process for synthesizing a substituted furanyl pyridine of formula II:

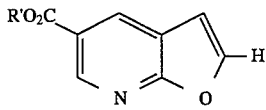

wherein

R' is $C_{1-4}$alkyl, or aryl;

comprising the steps of (a) providing one equivalent of the halogenated pyridine of the formula

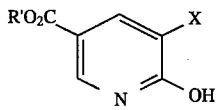

wherein X is Br, I, or Cl;

(b) reacting the halogenated pyridine of Step (a) with 1.0 or more equivalents of the acetylene

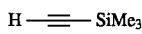

in the presence of catalyst selected from one or more of $Cu^I$, $Cu^{II}$, $Pd^0$, $Pd^{II}$, $Pt^0$, $Pt^{II}$, $Ni^0$, or $Ni^{II}$, in 1.0 or more equivalents of base and in ethereal or alcoholic solvent, at a temperature between about 25° C. and about 60° C., for a period of between about 30 minutes and about 48 hours;

(c) isolating the product

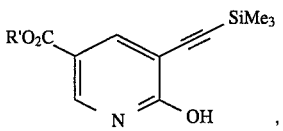

(d) reacting the product of Step (c) with in the presence of catalyst selected from $Cu^I$, $Cu^{II}$ or $Pd^{II}$ in ethereal solvent or in alcoholic solvent, at a temperature between about 25° C. and about 75° C. for an incubation time of between about 30 minutes and about 48 hours; and (e) treating with strong base or halide, at a temperature range of between about 25° C. and about 75° C. for an incubation time of between about 15 minutes and about 24 hours, to give a compound of formula II.

3. The process of claim 1 or 2, wherein for Step (d), the product of Step (c) is mixed with about 5 mole % CuI, suspended in $EtOH-Et_3N$ (7:3, v/v) and heated to about 72° C. for about 27 hours; and in Step (e) the strong base is $K_2CO_3$, and the reaction was carded out at about 65° C. for about 3.5 hours.

4. The process for synthesizing the furanyl pyridine ethyl ester of the formula

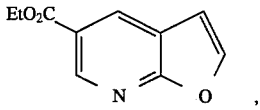

said process comprising the steps of (a) providing one equivalent of the 2-hydroxy pyridine of the formula

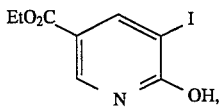

(b) reacting the pyridine of step (a) with about 1.1 to about 1.5 equivalents of the acetylene

in the presence of about 1 mole % $Pd^{II}$, about 2 mole % $Cu^I$, and about 2 mole % $PPh_3$, in about 2 equivalents of $n-BuNH_2$ in THF, at a temperature of between about 35° C. and about 39° C., for a period of between about 16 hr and about 27 hr, to give a silylacetylene intermediate;

(c) reacting the resulting intermediate with about 5 mole % $Cu^I$ in $EtOH-Et_3N$ (7:3, v/v) at about 70° C. for about 27 hr; and (d) treating the product of step (c) with $K_2CO_3$, (e) to give the desired furanyl pyridine ethyl ester.

5. The process for synthesizing the furanyl pyridine ethyl ester of the formula

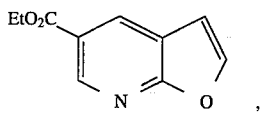

said process comprising the steps of (a) providing one equivalent of the 2-hydroxy pyridine of the formula

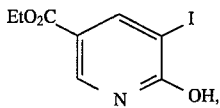

(b) reacting the pyridine of step (a) with about 1.1 to about 1.5 equivalents of the acetylene

H≡—TMS, in the presence of about 1 mole % $Pd^{II}$, about 2 mole % $Cu^{I}$, and about 2 mole % $PPh_3$, in about 2 equivalents of n-$BuNH_2$ in THF, at a temperature of between about 35° C. and about 39° C., for a period of between about 16 hr and about 27 hr, to give a silylacetylene intermediate;

(c) reacting the resulting intermediate with an excess of one equivalent of toluenesulfonic acid in THF at about 60° C. and for about 24 hr; and (d) treating the product of step (c) with $K_2CO_3$, (e) to give the desired furanyl pyridine ethyl ester.

* * * * *